United States Patent
Ikeda et al.

(10) Patent No.: US 6,741,350 B2
(45) Date of Patent: May 25, 2004

(54) PARTICLE SIZE DISTRIBUTION MEASURING APPARATUS WITH VALIDATION AND INSTRUCTION MODES

(75) Inventors: Hideyuki Ikeda, Kyoto (JP); Seiichiro Yoshioka, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/858,389

(22) Filed: May 16, 2001

(65) Prior Publication Data

US 2001/0048366 A1 Dec. 6, 2001

(30) Foreign Application Priority Data

May 16, 2000 (JP) ........................................ 2000-142963

(51) Int. Cl.⁷ .............................................. G01N 15/02
(52) U.S. Cl. ....................... 356/336; 356/337; 356/335; 356/343; 356/338
(58) Field of Search ................................ 356/335, 336, 356/343; 702/29

(56) References Cited

U.S. PATENT DOCUMENTS

| | | | | |
|---|---|---|---|---|
| 5,033,095 A | * | 7/1991 | Marcantonio | 382/112 |
| 5,380,663 A | | 1/1995 | Schwartz et al. | |
| 5,408,307 A | * | 4/1995 | Yamamoto et al. | 356/73 |
| 5,859,706 A | * | 1/1999 | Nagashima et al. | 356/394 |
| 5,867,273 A | * | 2/1999 | Corby, Jr. | 356/376 |
| 5,966,677 A | * | 10/1999 | Fiekowsky | 702/95 |
| 5,992,245 A | * | 11/1999 | Takei et al. | 73/865.5 |
| 6,091,492 A | * | 7/2000 | Strickland et al. | 356/336 |
| 6,236,458 B1 | * | 5/2001 | Igushi et al. | 356/336 |
| 6,252,658 B1 | * | 6/2001 | Togawa et al. | 356/335 |
| 6,263,744 B1 | * | 7/2001 | Russell et al. | 73/865.5 |
| 6,275,290 B1 | * | 8/2001 | Cerni et al. | 365/335 |
| 6,280,960 B1 | * | 8/2001 | Carr | 435/7.2 |
| 6,281,972 B1 | * | 8/2001 | Ebara et al. | 356/336 |
| 6,346,983 B1 | * | 2/2002 | Yufa | 356/338 |

FOREIGN PATENT DOCUMENTS

| | | |
|---|---|---|
| EP | 0 571 253 A2 | 11/1986 |
| JP | 03115950 | 5/1991 |
| JP | 06-249857 | 9/1994 |

OTHER PUBLICATIONS

Lohn A et al.: "A knowledge-based system for real time validation of calibrations and measurments", Chemometrics and Intelligent Laboratory Sytems, Elsevier Science Publishers, Amersterdam, NL, vol. 46, no.1, 15 Feb. 1999, pp. 57–66.

* cited by examiner

Primary Examiner—Michael G. Lee
Assistant Examiner—Ahshik Kim

(57) ABSTRACT

This invention provides a particle size distribution measuring apparatus, which has a function of informing an operator of a procedure of validation work of the particle size distribution measuring apparatus. A storage medium which records validation data providing a procedure of validation work for the particle size distribution measuring apparatus and a control unit which has a validation help function which successively reads a validation procedure from the validation data and controls the particle size distribution measuring apparatus according to a measuring procedure without any operation by an operator in the validation procedure while teaching the operator a work procedure requiring an operation by the operator.

14 Claims, 16 Drawing Sheets

FIG. 13

| | |
|---|---|
| SP Area | :10823(cm²/cm³) |
| Median | :5.5438(μm) |
| Mean | :5.5438(μm) |
| Variance | :0.000(μm²) |
| S.D. | :0.000(μm) |
| CV | :0.000 |
| Mode | :5.5438 |

| | |
|---|---|
| File name | :08146121121200 |
| ID # | :20001212124608I |
| Circulation Speed | :OFF |
| Ultra Sonic | :OFF |
| Laser T% | :0.0(%) |
| Form of Distribution | :Manual |

Axis Section    Log X-Lin Y

Data files

Test Data

P0080a01.d2w     WA2000+ UB223Ld2w
US5min.d2w       WA2000+ UB223L_2.d2w
w0013.d2w        WA    (TP).d2w
w1315.d2w
w22230N.d2w
wa20000.d2w Name (N)
Type of file(T)  LA WET System & LB Data format
Memory  DEFAULT

OPEN (O)   SAVE (S)   TYTLE (T)   CANCEL (C)

100.0

0.0

0.100    1.000    10.00    100.00    600.00
Diameter (μm)

PARTICLE SIZE DISTRIBUTION MEASURING APPARATUS WITH VALIDATION AND INSTRUCTION MODES

BACKGROUND OF THE INVENTION

1. Field of the Invention

The present invention relates to a particle (grain) size measuring apparatus, which detects a diffraction/scattered light or dynamic light scattering by irradiating a laser beam onto a particle group such as a dispersing powder sample or the like, and measures a particle size distribution of the particle group on the basis of a scattered light intensity signal or the like obtained by the detection and more particularly provides an automatic validation and instruction mode.

2. Description of the Prior Art

Conventionally, a particle size distribution measuring apparatus using a light diffraction phenomenon or scattering phenomenon by a particle has calculated a particle size distribution of a sample particle in the following manner. More specifically, the above apparatus measures intensity distribution of a diffraction light or a scattered light, that is, a relation between a diffraction angle or scattering angle and a light intensity, and then, carries out arithmetic processing based on a Frauunhofer diffraction theory or Mie scattering theory with respect to the measured result. In the above manner, the above apparatus has calculated the particle size distribution of a sample particle. The above particle size distribution measuring apparatus has been used for research and development of raw materials in most mining and industrial fields such as the cement or the ceramic industry, and in a new material field mainly using ceramics.

For example, to give an example of the above apparatus, there is a particle size distribution measuring apparatus disclosed in Japanese Examined Patent publication No. 6-43950. FIG. 16 is a view schematically showing a construction of the particle size distribution measuring apparatus disclosed in this Publication. In FIG. 16, a reference numeral 10 denotes a cell comprising a transparent container for receiving a sample solution 11 dispersing a particle group of the measuring object in a proper dispersion medium, and a reference numeral 12 denotes a laser beam source provided on one side (backward side) of the cell 10. A parallel laser beam 13 emitted from the laser beam source 12 is enlarged by a beam expander (not shown), and then, is irradiated to the cell 10 in an enlarged state.

In FIG. 16, a reference numeral 14 denotes a condenser lens provided on the other side (forward side) of the cell 10, and a ring detector 15 is arranged at a focal position of the condenser lens 14. The ring detector 15 is constructed in a manner that a plurality of photo sensors having mutually different radii and a ring or semi-ring light receiving plane is arrayed concentrically around an optical axis of the condenser lens 14. Further, the ring detector 15 receives light scattered/diffracted at a relatively small angle to the optical axis of the laser beam 13 diffracted or scattered by particles in the cell 10 for each scattering angle, and then, measures their light intensity.

Moreover, a wide angle scattered light photo detector group 16 is provided at the vicinity of the cell 10. The wide angle scattered light photo detector group 16 individually detects light scattered/diffracted at a relatively large angle to the optical axis of the laser beam 13 diffracted/scattered by the particles in the cell 10 for each scattered light. Further, the wide angle scattered light photo detector group 16 is composed of a plurality of photo sensors 17 to 22 provided at an angle different from the condenser lens 14 and the ring detector 15. Thus, the photo detector group 16 can detect a wide angle scattered light exceeding a predetermined angle by the particles in the cell 10 in accordance with each oriented angle. In the photo detector group 16, the photo sensors 17 to 20 detect a forward scattering light, the photo sensor 21 detects a side scattering light, and the photo sensor 22 detects a backscattering light.

A reference numeral 23 denotes a pre-amplifier for amplifying an output of the photo sensors constituting the ring detector 15, and a reference numeral 24 denotes a pre-amplifier for amplifying each output of the forward scattering light photo sensors 17 to 20. Further, a reference numeral 25 denotes a pre-amplifier for amplifying each output of the side scattering light photo sensor 21 and the backscattering light photo sensor 22. A reference numeral 26 denotes a multiplexer for successively capturing each output of the pre-amplifier groups 23 to 25 and transmitting it to an A-D converter 27, and a reference numeral 28 denotes a computer which is used as an arithmetic processor for inputting an output from the A-D converter 27. The computer 28 stores a program for processing each output converted into a digital signal (digital data relative to light intensity) of the ring detector 15 and the photo sensors 13 to 22 on the basis of a Frauunhofer diffraction theory or Mie scattering theory, and obtaining a particle size distribution in a particle group.

In the above particle size distribution measuring apparatus, in a state that the sample solution 11 is received in the cell 10, when the laser beam 13 is irradiated from the laser beam source 12 to the sample cell 10, the laser beam 13 is diffracted or scattered by the particles in the cell 10. Of the diffracted light or scattered light, a light having a relatively small scattering angle is imaged on the ring detector 15 by the condenser lens 14. In this case, the photo sensor arranged on the outer side receives a light having a larger scattering angle; on the other hand, the photo sensor arranged on the inner side receives a light having a smaller scattering angle. Therefore, a light intensity detected by an outer-side photo sensor means a quantity of particles having smaller particle diameter (particle size); on the other hand, a light intensity detected by the inner-side photo sensor means a quantity of sample particles having larger particle diameter. The light intensity detected by each of these photo sensors is converted into an analog electric signal, and further, is inputted to the multiplexer 26 via the pre-amplifier 23.

On the other hand, of the laser beam 13 diffracted light or scattered by the particles, a light, which is not converged by the condenser lens 14 and has a relatively large scattering angle, is detected by the photo sensors 17 to 22, and then, its light intensity is measured. In this case, the forward scattering light photo sensors 17 to 20, the side scattering light photo sensor 21 and the backscattering light photo sensor 22 successively detect a scattering light from a particle having a small particle size. The light intensity detected by each of these photo sensors 17 to 22 is converted into an analog electric signal, and further, is inputted to the multiplexer 26 via the pre-amplifier groups 24 and 25.

The multiplexer 26 captures measurement data from the ring detector 15 and the photo sensors 17 to 22, that is, an analog electrical signal in a predetermined order. The analog electric signal captured by the multiplexer 26 is made into a serial signal, then, is converted by the A-D converter 27 into a digital signal in succession, and thereafter, is inputted to the computer 28.

Subsequently, the computer 28 processes the light intensity data for each scattering angle obtained by each sensor of the ring detector 15 and the photo sensors 17 to 22 on the basis of a Frauunhofer diffraction theory or Mie a scattering theory.

As described above, in the above particle size distribution measuring apparatus, a light intensity distribution of scattering light having a substantially larger particle size is measured by the ring detector 15 and a light intensity distribution of wide-angle scattering light having a mainly smaller particle size is measured by the photo sensors 17 to 22. Further, the output of these ring detector 15 and photo sensors 17 to 22 is processed by the computer 28. Therefore, it is possible to obtain a particle size distribution of particle group over a wide range from a relatively larger particle size to a micro particle size.

By the way, the particle size distribution measuring apparatus as described above requires periodically carrying out a validation work in order to make a decision whether or not its measuring accuracy is correctly made. In particular, in a pharmaceutical company, in the case where the above particle size distribution measuring apparatus is used for a quality control, the validation work must be correctly done at least once per year.

In order to correctly do the validation of the particle size distribution measuring apparatus, an operator must measure a predetermined standard sample according to a determined procedure. For this reason, in the conventional particle size distribution measuring apparatus, the operator prepares a validation manual recording procedures of the above validation work, and then, must carry out the validation work according to the determined procedures.

However, a measuring technique using the above particle size distribution measuring apparatus is complicated, and therefore, it is difficult for an inexperienced operator to memorize and operate all of the working procedures. For this reason, in the case where an inexperienced operator operates the above apparatus, the operator must operate a control unit while referring to a user manual. In fact, when an inexperienced operator performs the above operation while referring to a user manual, such an operator can easily make a mistake in the sequence of work, and may not notice the mistake. Therefore, validation cam be incorrectly carried out; and for this reason, the resulting numerical value has no reliability.

In such a case, the measurement procedure must be performed again. However, in order to again make a measurement, the following steps are required. More specifically, dispersion medium and standard sample in a sample supply apparatus are discharged, and the sample supply apparatus is washed, and thereafter, the dispersion medium and standard sample are charged in the supply apparatus. Excessive time and labor are spent for doing the above work, and in the case where the standard sample is valuable, there is a possibility that many standard samples are wasted.

After the validation work is completed, the operator makes a report based on the measurement result, and must store the report; however, there is the case where the operator forgets this work. For this reason, there is a problem that no record is stored in spite of carrying out the validation work.

In addition, the above scattering type particle size distribution measuring apparatus uses precision optical components, a laser beam source, a motor and the like; for this reason, there is a possibility that an accident happens in the case where a user disassembles the apparatus in error, or makes a handling mistake. In order to prevent such an accident, conventionally, caution procedures have been prescribed in a manual or the like, or a label describing handling caution matters have been stuck onto the apparatus main body. However, the aforesaid accident happens due to a user's careless mistake and an erroneous operation by an inexperienced operator; for this reason, there is a possibility that the number of processes may be required on a maker side or user side.

The present invention has been made in view of the aforesaid problems in the related art. It is, therefore, an object of the present invention to provide a particle size distribution measuring apparatus, which has a function of informing an operator of a procedure of validation work of the particle size distribution measuring apparatus, and thereby, can prevent a generation of mistake in a complicated validation work.

SUMMARY OF THE INVENTION

In order to achieve the above object, the present invention provides a particle size distribution measuring apparatus comprising: a storage medium which records a validation data indicating a procedure of validation work for a particle size distribution measuring apparatus, and a control unit which has a validation help function which successively reads a validation procedure from the validation data and successively carries out a control for the particle size distribution measuring apparatus according to a measuring procedure requiring no operation by an operator in the validation procedure while teaching the operator a work procedure requiring an operation by the operator.

Therefore, when carrying out the validation work, the operator can use the validation help function, and thereby, can operate the particle size distribution measuring apparatus according to the work procedure given from the control unit in a predetermined order without making a mistake. Moreover, the measuring procedure which is controlled by only a control unit is automatically carried out, by which the control unit controls the particle size distribution measuring apparatus according to an operation sequence previously stored as validation data.

The measuring procedure automatically carried out by the control unit includes a procedure for setting a setup value of a measuring object sample such as a refractive index of a standard sample used for the validation work. Therefore, the operator has no need of carrying out troublesome various setup operations for the validation work.

Accordingly, the operator can perform the complicated validation work without referring to a manual, and thereby, it is possible to reduce the responsibility of the operator to the minimum, and to successively carry out the work procedure made by the operator step by step without making a mistake. This serves to more accurately perform the validation work.

In the case where the control unit has a warning function of pointing out the operator's mistake in the work procedure to the operator, and teaching a proper validation work according to a correct work procedure, when the operator makes an erroneous operation, a warning is given from the control unit. Therefore, the validation work is accurately performed, so that a measured result having a high reliability can be obtained.

The following matter is considered as a possible aforesaid mistake in the work procedure; more specifically, the operator charges a standard sample unsuitable for the measurement condition. For example, it is considered that concentration and temperature of the charged sample are outside a range of measurement condition predetermined as a standard sample. In this case, the concentration of the sample is previously measured by a light transmittance, and then, in the case where the measured result is different from the sample concentration condition, the control unit can give an instruction to adjust the concentration of the sample to the operator. Moreover, the control unit may have a warning function which confirms the measurement condition during measurement of particle size distribution, and gives an instruction to the operator to retry the measurement in the case where the measurement condition is beyond a range of a predetermined value.

In the case where the control unit has a speech (voice) output section for outputting an instruction to the operator by a speech signal, an operating instruction is given by machine generated speech; therefore, the operator can readily perform a validation work according to the spoken instruction without giving attention to reading a manual and the like.

In the case where the control unit has a monitor screen for displaying an instruction to the operator, the operator can obtain instructions for validation work via a display screen; therefore, it is possible to readily perform the validation work.

Moreover, in the case where the particle size distribution measuring apparatus of the present invention has an automatic charger for successively charging a standard sample used for the validation work into the above particle size distribution measuring apparatus, it is possible to reduce the work done by the operator to the minimum, and further, to easily handle the above apparatus. In this case, preferably, the control unit has a function of continuously measuring a plurality of standard samples.

The control unit has a judgment function of comparing an inspection result obtained from the validation work with a performance standard of the particle size distribution measuring apparatus, and making a judgment whether or not the comparative result is within the performance standard range. In this case, the operator has no need of collating the comparative result with a standard chart of the particle size distribution measuring apparatus, and making a judgment whether or not an error is within the performance standard range.

In the case where the control unit has a recording function of recording the inspection result obtained by the validation work, the inspection result is automatically stored after the validation work is performed. Even in the case where the operator forgets the output of the inspection result, it is possible to prepare a report using records of the inspection result automatically stored. Therefore, the record is not lost when carrying out the validation work. In this case, the record of the inspection result may be a result data stored in the storage medium, or may be an inspection result report outputted by a printer or the like.

BRIEF DESCRIPTION OF THE DRAWINGS

FIG. 13 is a view showing another display window on the screen;

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein to specifically provide a particle size distribution measuring apparatus with validation and instruction modes of operation.

One embodiment of the present invention will be described below with reference to the accompanying drawings.

Figure 1:
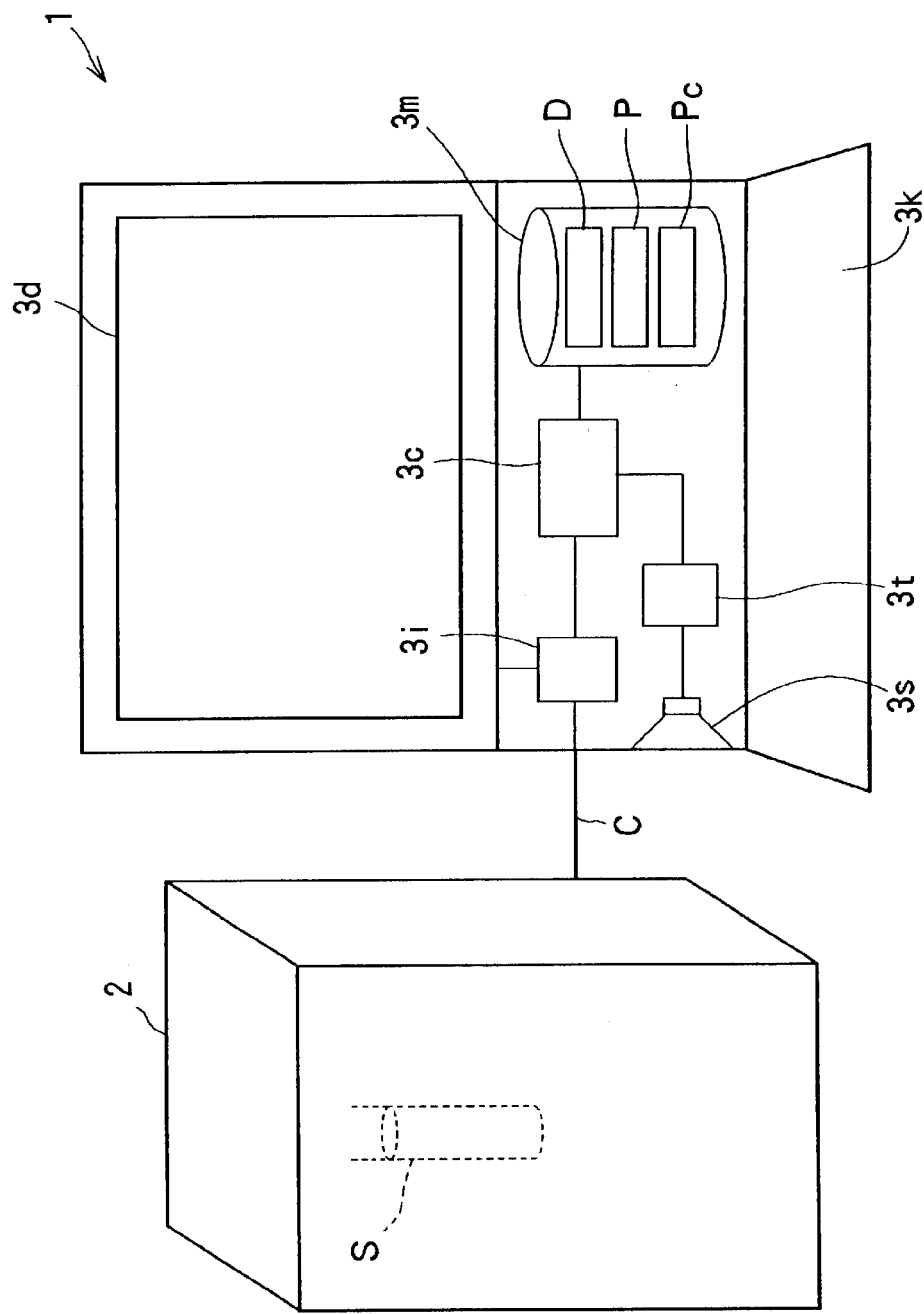
FIG. 1 is a view schematically showing a construction of a particle size distribution measuring apparatus according to one embodiment of the present invention.

In FIG. 1, a particle size distribution measuring apparatus 1 of this embodiment has a measuring section 2 for measuring a particle size distribution of a measuring object sample S, and a control unit 3 connected to the measuring section 2. In the measuring section 2, a laser beam is irradiated to the measuring object sample S charged from a charging hole so as to detect a scattered light by particles in the measuring object sample S, and then, the scattered light is analyzed, and thereby, its particle size distribution is measured.

In this embodiment, the control unit 3 is an information processing unit (hereinafter, referred to as a personal computer 3), which is connected to the measuring section 2 via a communication cable C. The control unit 3 has a display 3d (i.e., monitor screen) and a keyboard 3k. However, in the present invention, the construction of the control unit 3 is not limited to this embodiment. For example, the control unit 3 may be a microcomputer provided in the measuring section 2.

The aforesaid personal computer 3 has a CPU 3c, a storage (memory) section 3m such as a RAM, a ROM, a hard disk or the like, and an input-output interface 3i. The storage section 3m previously stores a control program Pc, and controls the measuring section 2 by executing the control program Pc. More specifically, the personal computer 3 executes various arithmetic processings on the basis of a data inputted from the input-output interface 3i, and outputs the processing (output) result via the input-output interface 3i.

Moreover, the input-output interface 3i is connected with the communication cable C so that a signal from sensors (not shown) incorporated into each part of the measuring section 2 can be transmitted to the personal computer main body via the communication cable C.

The storage section 3m stores a validation program P and a validation data D decoded by the validation program P, in addition to the above control program Pc. More specifically, the personal computer 3 has a validation help function by the control program Pc, the validation program P and the validation data D.

In this embodiment, regardless of the validation work, the validation program P is executable by reading a control data (including the above validation data D) recorded by a simple language for controlling the measuring section 2, and thereby, the validation program P has a general-purpose characteristic.

Further, the validation program P automatically and successively carries out a procedure executable in the particle size distribution measuring apparatus 1, to provide the procedures of validation work recorded as the validation data D. Meanwhile, regarding a procedure requiring an operation by the operator, the validation program P is programmed so as to give a work instruction relative to the procedure to the operator. As a result, the operator merely carries out a necessary and minimum operation, so that the validation work can be simplified.

The work instruction to the operator is outputted by a message on display screen 3d and a voice announcement. More specifically, in the case of carrying out a validation work, the operator has no need of reading a manual describing a working procedure for the validation, and can perform the validation work according to a message display on the display screen 3d or the announced instruction; therefore, the operator is able to concentrate on the validation work.

The validation data D includes at least one of an announcement by recorded speech and a message displayed on the display screen. For example, in the case of carrying out an announcement by audio speech, the personal computer 3 has a converter 3t for converting digital data stored as validation data D into a speech (audio) signal, and a speaker 3s which is a speech output section.

The validation program P is programmed in a manner that a work situation of the operator is detected and grasped by a sensor incorporated into each part of the measuring section 2. In the case where the operator makes a mistake in the work procedure, the validation program P is programmed in a manner of giving a warning to the operator, and giving an instruction for carrying out the validation work according to a correct work procedure to the same.

The following matter is considered as an example of a possible mistake in the work procedure; more specifically, the measuring object sample S charged into the measuring section 2 by the operator is beyond a range of concentration usable as a standard sample. In this case, it is possible to use a sensor for measuring a light transmittance of the measuring object sample S. Moreover, in the case where the inexperienced operator makes a mistake of handling the measuring section 2 by his careless or erroneous operation, a warning can be given to the operator. More specifically, when the operator opens a cover of the apparatus, which should not be opened during measurement work, the following announcement or message is made or displayed; for example, "Please close the cover. Please do not look at laser beam source in the apparatus."

Figure 2:
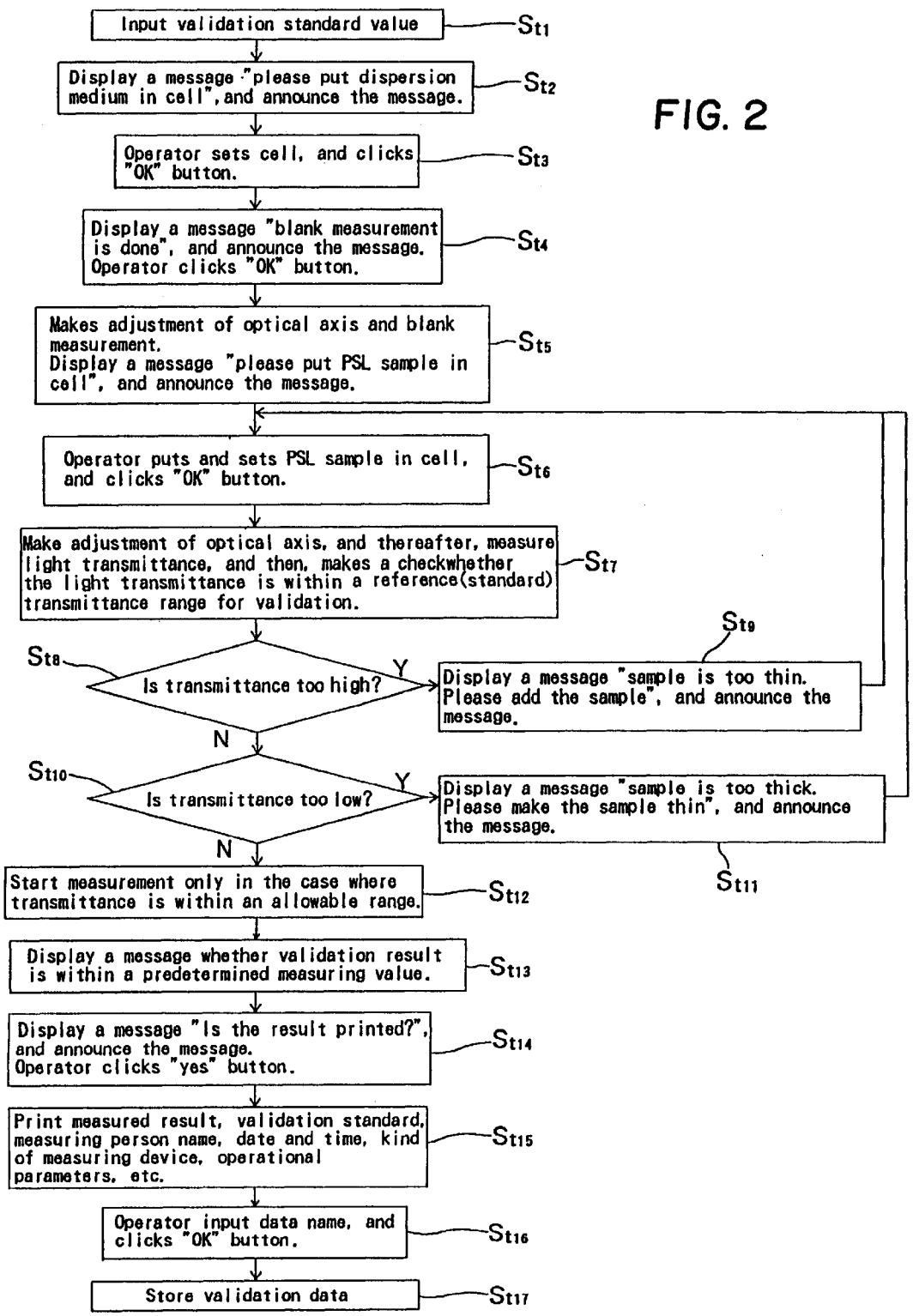
FIG. 2 is a view to explain an operation of validation help function of the above embodiment.

FIG. 2 is a flowchart showing a procedure of the validation work in this embodiment, and shows measuring and operating procedures. FIG. 3 to FIG. 13 are views showing examples of window screens displayed on the display 3d pursuant to the progress of the validation work.

In FIG. 2, step $S_{t1}$, shows one example of an operation previously executed before the validation data D is read and the validation program P is executed. Namely, the operator presets validation standards.

Figure 3:
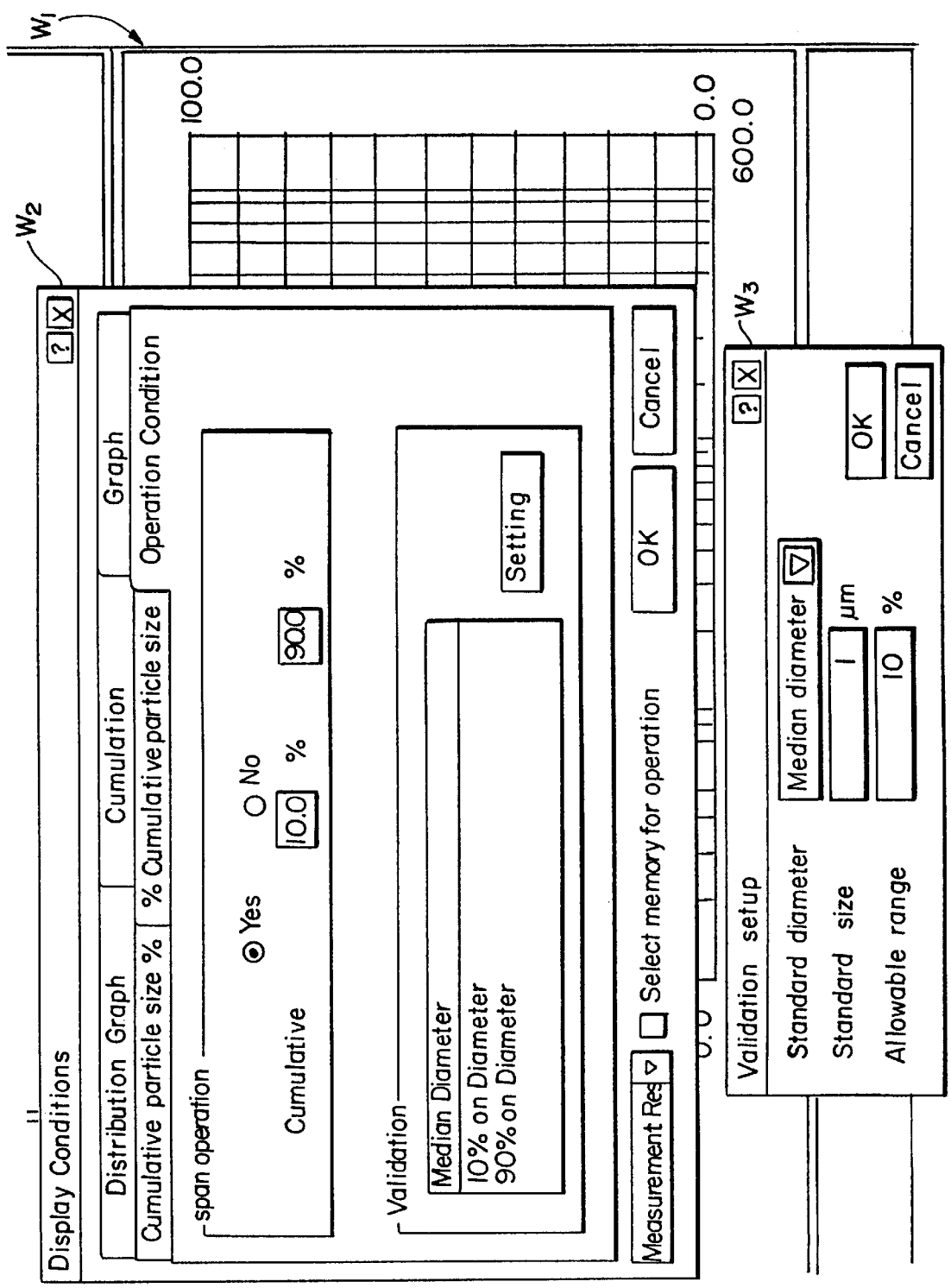
FIG. 3 is a view showing a display window on a screen when measuring a standard sample using the validation help function of the particle size distribution measuring apparatus.
Figure 4:
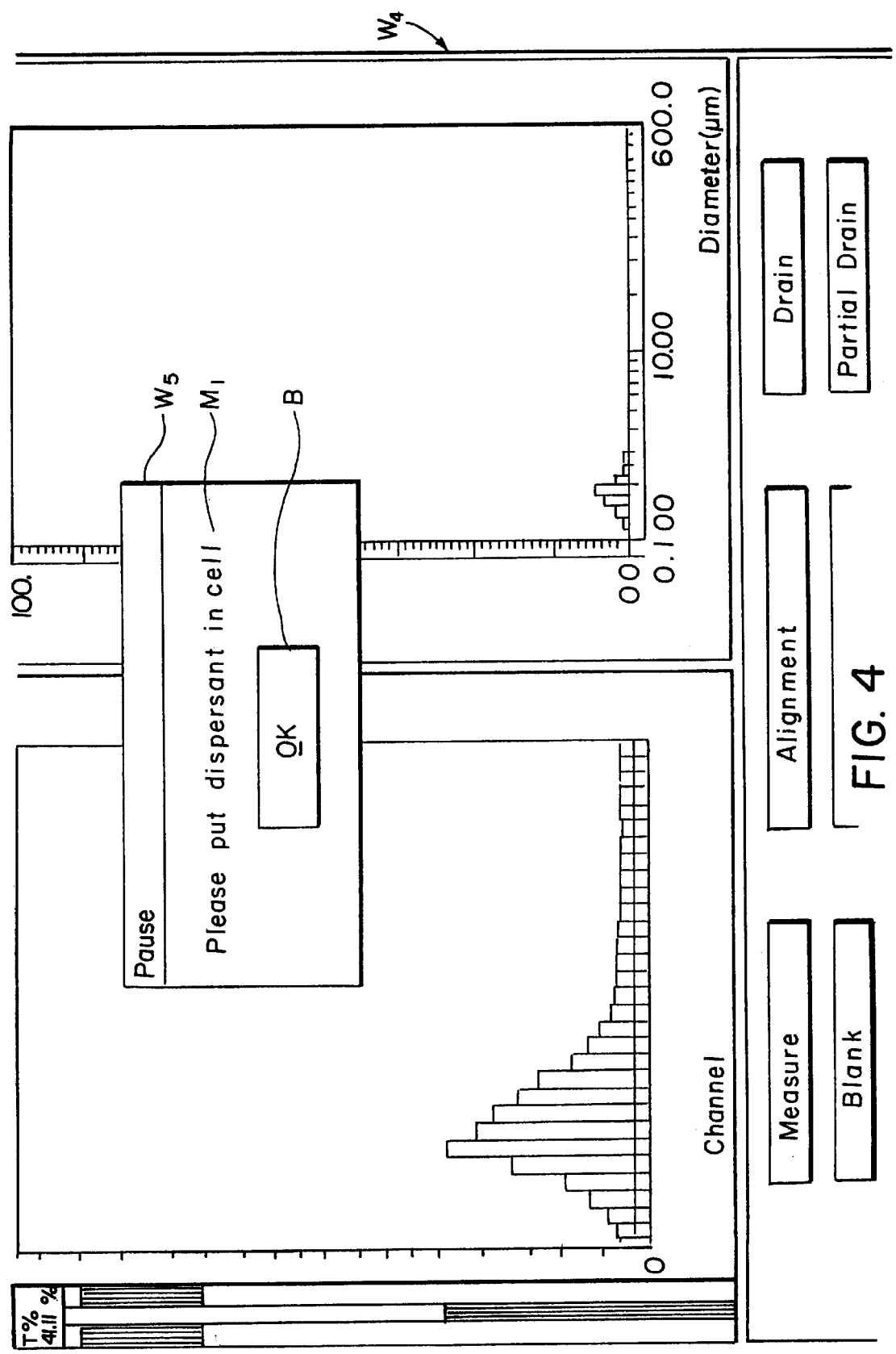
FIG. 4 is a view showing another display window on the screen.

FIG. 3 is a view showing a window displayed on the display 3d of the personal computer 3 in the above step $S_{t1}$.

In FIG. 3, $W_1$, is a main window, and $W_2$ is a display condition setup window. When seeing the display condition setup window $W_2$, in this embodiment, it is possible to input standard values relative to three kinds of diameters (median diameter, 10% diameter, 90% diameter) with respect to one standard sample. $W_3$ is a validation setup window for setting validation judgment factors such that each standard diameter has a set size ($\mu$m) or a permissible error in the size of diameter is applicable by what percents in plus and minus as an allowable range.

More specifically, in this embodiment, three kinds of standard diameters are set with respect to one standard sample, and then, in each diameter, a judgment is made whether or not the measured value is within a permissible error range; therefore, it is possible to perform a more detailed validation work. In the present invention, the number of diameters set as the validation standard diameter is not limited to three. For example, only a standard value and an allowable range relative to median diameter may be set.

The judgment standard of validation work set in the above manner is reflected in the validation data D. Namely, the operator can freely change the judgment standard of validation work. Likewise, the operator can freely change a kind of standard sample used in the validation work and physical information such as a refractive index of the standard sample or the like.

In the following embodiment, a PSL (Polystyrene latex) sphere having a diameter of 1 $\mu$m is used as the standard sample. Moreover, various data such as a kind and allowable range of the standard sample may be predetermined as the judgment standard of validation work by a maker of the particle size distribution measuring apparatus.

Next, when the validation program P starts up, the validation program P reads the validation data D, and then, successively executes various processings based on the validation data D.

In Step $S_{t2}$ shown in FIG. 2, the personal computer 3 displays a measuring window $W_4$ on the display screen, and further, displays a message window $W_5$ thereon. Moreover, in a message window $W_5$, a message $M_1$ "Please put dispersion medium in cell" is displayed, and thereafter, the same announcement as the message $M_1$ is converted into speech, and outputted from the speaker.

Subsequently, the operator sets a cell, into which distilled water is put as a dispersion medium, in the measuring section 2, and thereafter, operates an OK button B displayed on the message window $W_5$ (step $S_{t3}$). In this case, a method for operating the OK button B is as follows. For example, in the case of a keyboard, the OK button B is selected by a cursor key, and thereafter, a return key is pressed. Moreover, in the case of a mouse, the mouse is clicked in a state of bringing the cursor key to the OK button B. In order to simplify the description, the operation as described above is referred simply to "press the OK button".

In this embodiment, the personal computer 3 senses the completion of work when the operator presses the OK button B; however, the present invention is not limited to this embodiment. More specifically, the completion of work may be sensed by a sensor attached to each part of the measuring section 2.

Next, the personal computer 3 reads the following procedure from the validation data D, and then, executes the procedure. The next procedure of validation work is blank measurement, and is a measuring procedure executable in the particle size distribution measuring apparatus 1 without requiring any work by the operator. Therefore, after waiting for the operator's instruction, the personal computer 3 automatically controls each part of the measuring section 2, and then, executes the blank measurement.

Figure 5:
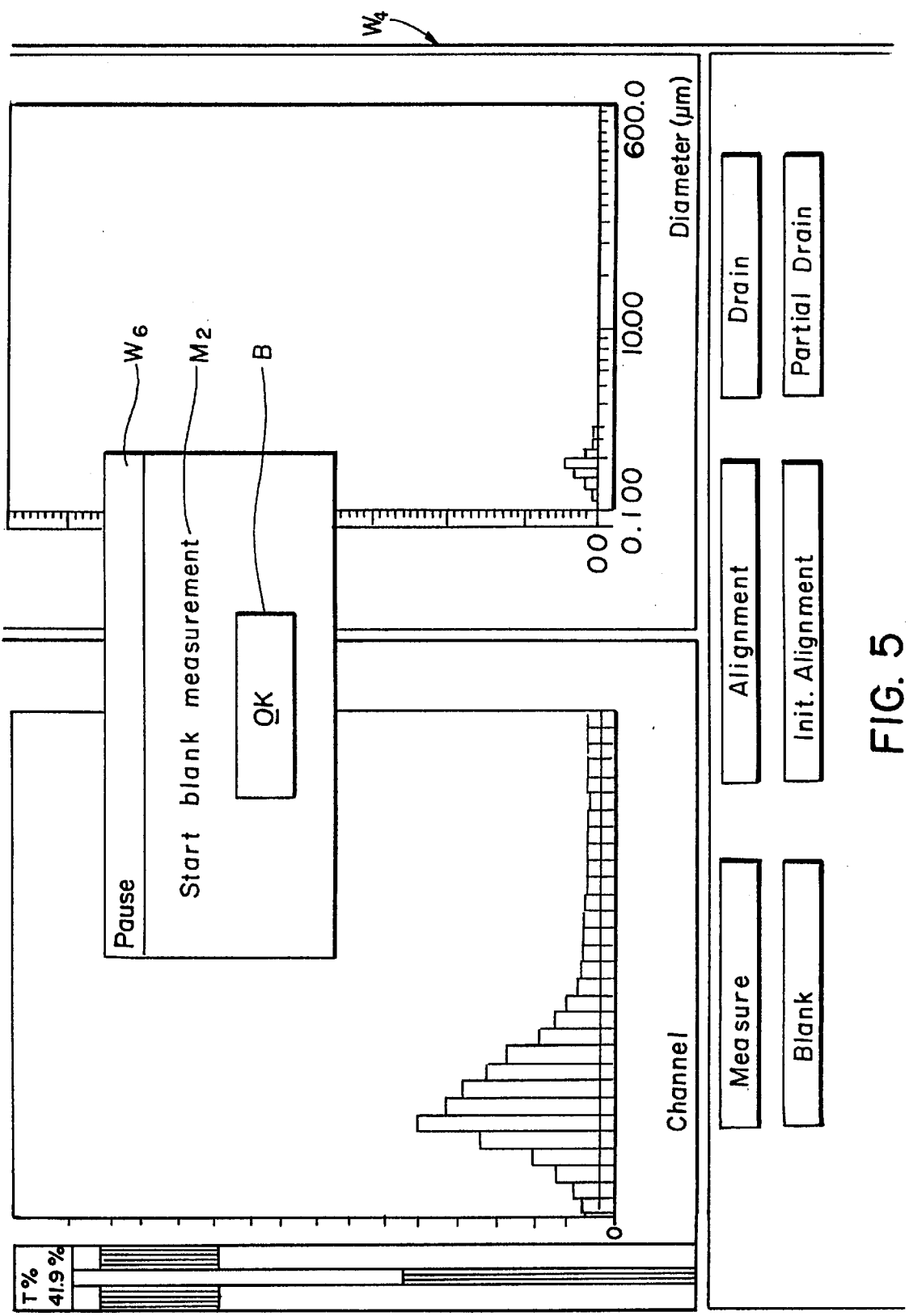
FIG. 5 is a view showing another display window on the screen.

FIG. 5 shows a message window $W_6$. In this message window $W_6$, a message $M_2$ "execute blank measurement" is displayed, and the personal computer 3 is waiting for the operator to press the OK button B while making announcement of the above message $M_2$ (step $S_{t4}$).

Subsequently, when the OK button B is pressed, the personal computer makes an adjustment of an optical axis according to the measuring procedure shown by the validation data D, and thereafter, executes a blank measurement. In this case, the personal computer 3 is controlled by the validation program P, and each part required for the blank measurement is automatically adjusted; therefore, the operator has no part in any of the operations.

Figure 6:
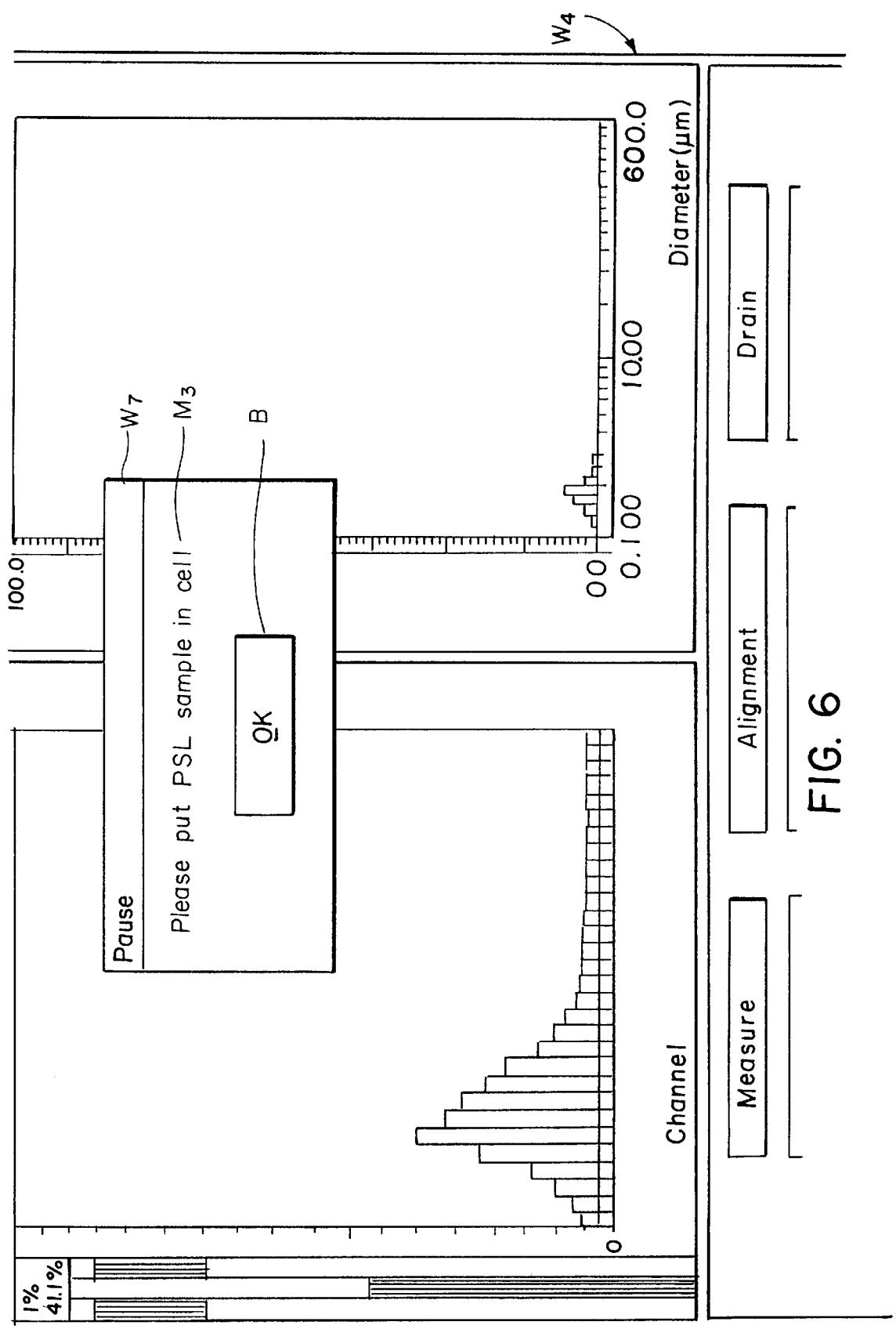
FIG. 6 is a view showing another display window on the screen.

When the blank measurement is completed, the personal computer 3 again reads the validation data D, and then, executes the next validation work. The next validation work is a work procedure on which the operator puts the standard sample S in the cell. For this reason, the personal computer 3 displays a message window $W_7$ as shown in FIG. 6. In the message window $W_7$, a message $M_3$ for instructing the work procedure to the operator is displayed, and a speech of the same content as the message $M_3$ is announced (step $S_{t5}$).

Subsequently, the operator mixes a PSL sphere in the cell according to the above message $M_3$, and then, inputs the completion of work by pressing the OK button B (step $S_{t6}$).

Then, the personal computer 3 reads the validation data D so as to execute the next validation work. More specifically, as shown in step $S_{t7}$, the personal computer 3 executes an adjustment of the optical axis, and thereafter, measures a light transmittance in order to confirm whether or not a measuring object sample put in by the operator has a transmittance within a range predetermined as a standard sample S for validation.

Namely, a decision is made whether or not the light transmittance of the measuring object sample S is higher than the upper limit of a predetermined transmittance (step $S_{t8}$).

Figure 7:
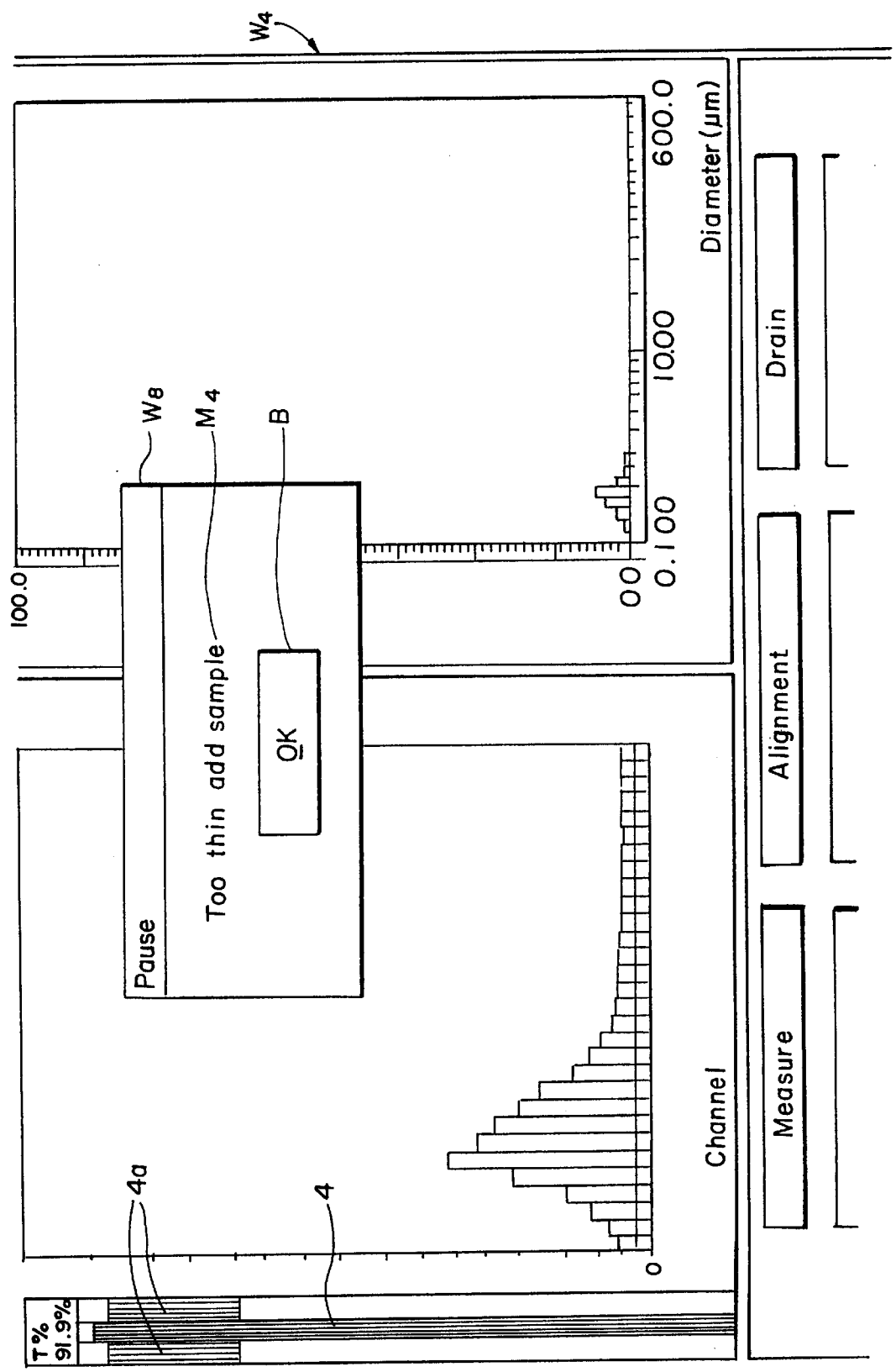
FIG. 7 is a view showing another display window on the screen.
Figure 8:
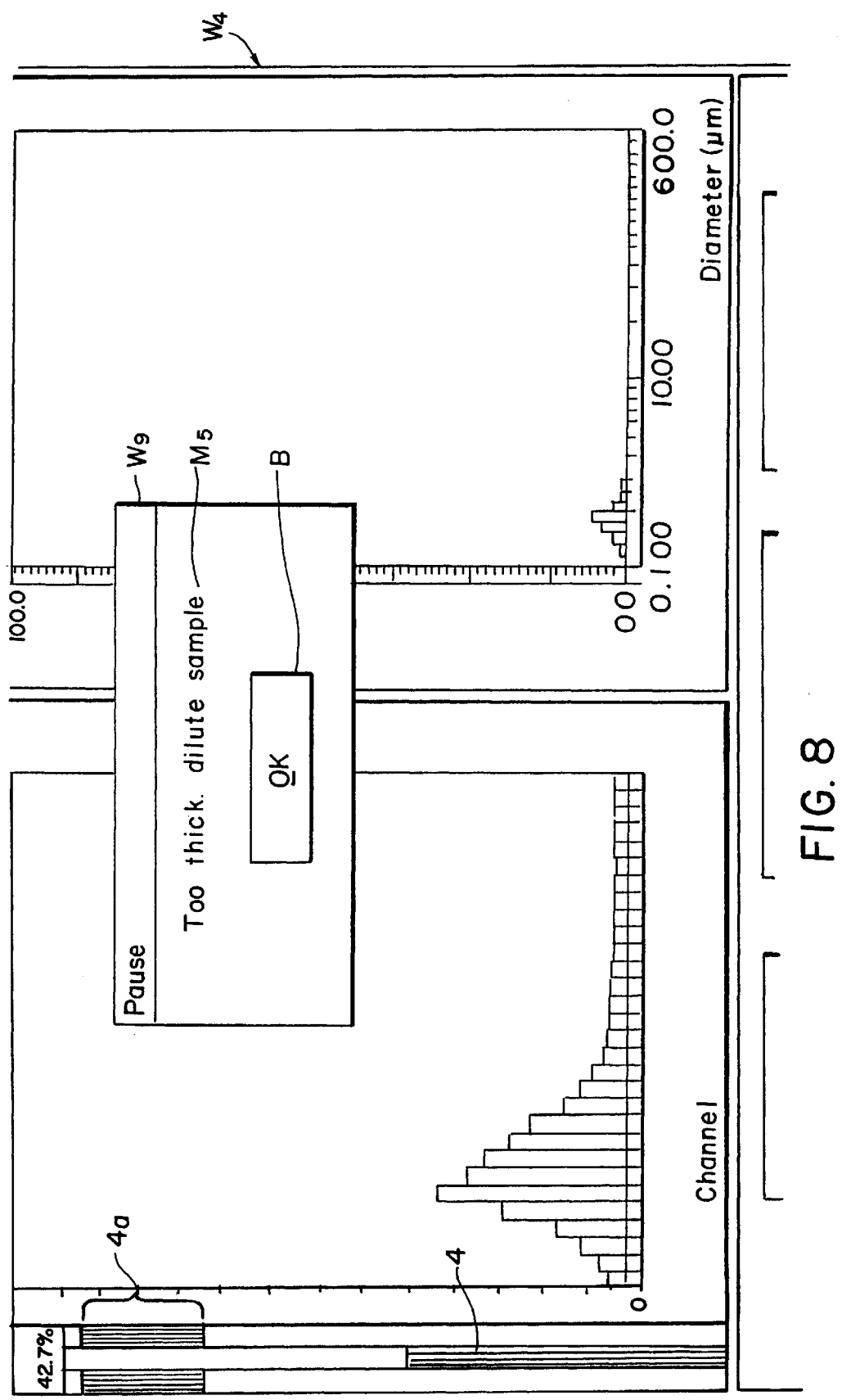
FIG. 8 is a view showing another display window on the screen.
Figure 9:
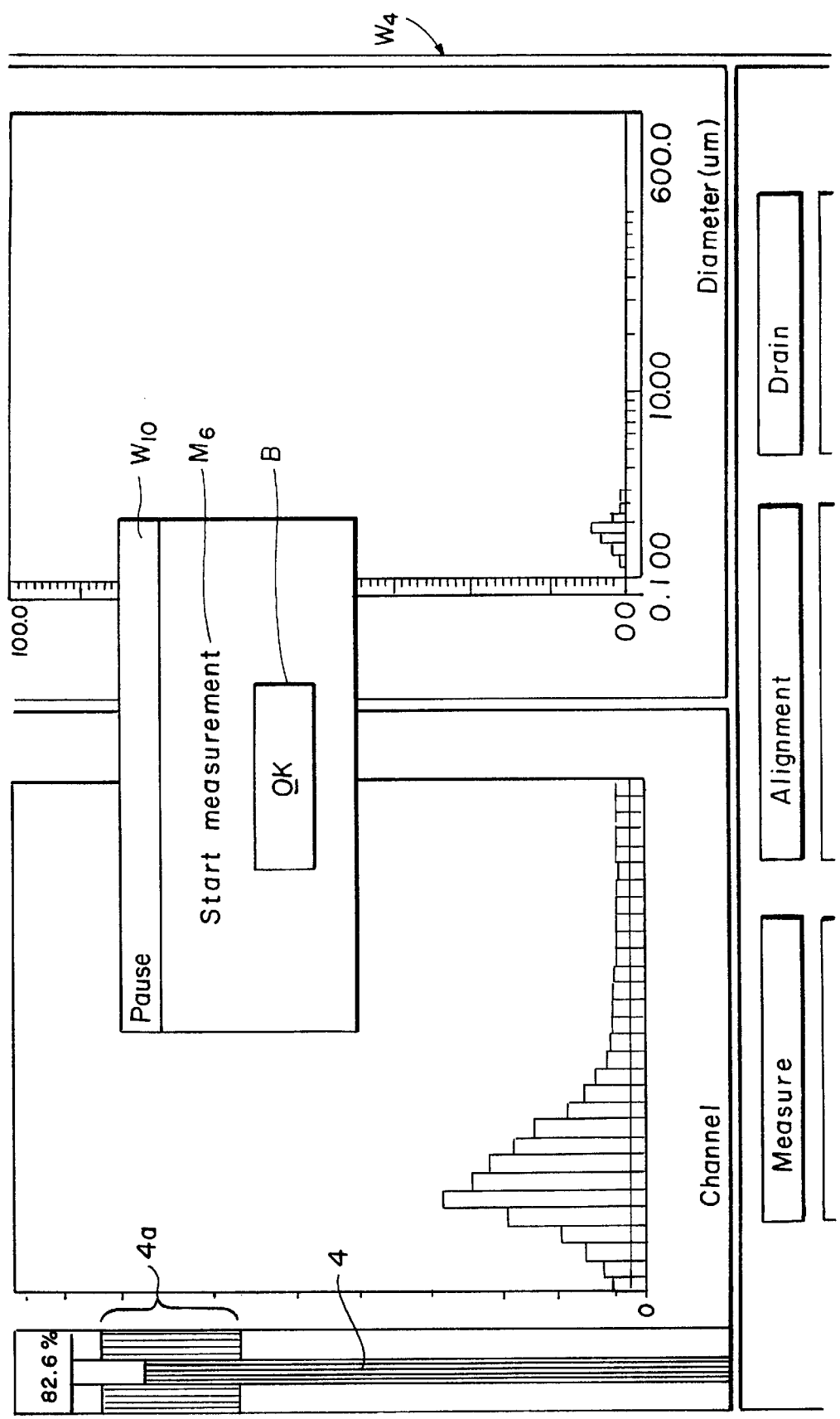
FIG. 9 is a view showing another display window on the screen.

At that time, in the case where the transmittance is too high, as shown in FIG. 7, a message window $W_8$ is displayed, and a message $M_4$ "concentration is too thin. Please add sample thereto" is displayed on the window screen while an announcement by speech is being outputted. In FIG. 8 and FIG. 9 described later, a reference numeral 4 denotes a bar graph showing a light transmittance measured in the above step $S_{t8}$, and a reference numeral 4a denotes a predetermined range of the light transmittance. When the operator presses the OK button B, the validation work is returned to step $S_{t6}$, and then, measurement for the light transmittance can be retried (step $S_{t9}$).

On the other hand, in the case where the light transmittance 4 of the measuring object sample S is not higher than the upper limit of the predetermined transmittance range 4a, conversely, a decision is made whether or not the light transmittance of the measuring object sample S is lower than the lower limit of predetermined transmittance range 4a (step $S_{t10}$).

In the case where the light transmittance 4 is too low, as shown in FIG. 8, a message window $W_9$ is displayed, and a message $M_5$ "concentration is too strong. Please make sample thin" is displayed on the window screen while an announcement by speech is also being outputted. When the operator presses the OK button B, the validation work is returned to step $S_{t6}$, and then, measurement for the light transmittance can be retried (step $S_{t11}$).

In the above manner, in the case where the light transmittance 4 is set within the predetermined range 4a, as shown in FIG. 9, a message window $W_{10}$ is displayed, and a message $M_6$ "Start measurement" is displayed on the window screen while an announcement by speech is being outputted. Then, when the operator presses the OK button B, a measurement of the particle size distribution is started (step $S_{t12}$).

In this case, the personal computer 3 automatically executes the following various settings for the particle size distribution measuring apparatus according to the measurement procedure recorded as the validation data D. The various settings include an input of refractive index of the standard sample S and solvent required for measuring a particle size distribution, etc. Namely, the operator has no need of doing troublesome various setting steps for the validation work. Moreover, it is possible to prevent a mistake which could be made in the case where the operator does the above various settings manually, and therefore, even an inexperienced operator can confidently perform the validation work.

Subsequently, when the particle size distribution measurement is completed, the personal computer 3 displays the measured result on windows Wa to Wc according to the measurement procedure recorded as the validation data D, and thereafter, makes a decision whether or not the measured result is suitable. Namely, the personal computer 3 makes a decision whether or not the measured result of the particle size distribution measuring apparatus 1 is within an allowable error range.

Figure 10:
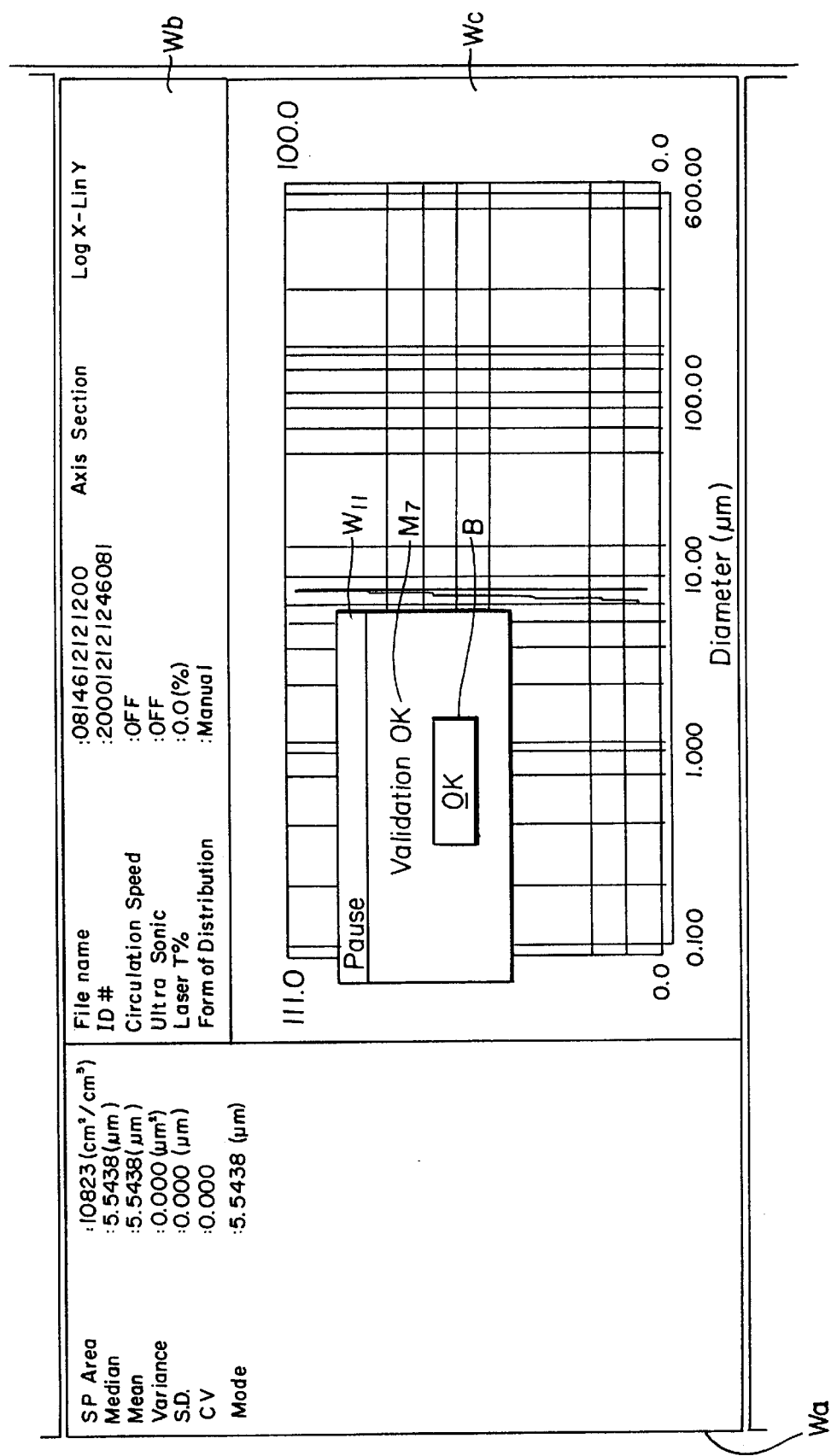
FIG. 10 is a view showing another display window on the screen.

Then, the personal computer 3 displays a message window $W_{11}$, as shown in FIG. 10 in the case where the above measured result is within an allowable range, and displays a message $M_7$ "Validation OK" on the window screen while outputting an announcement by speech. On the other hand, in the case where the above measured result is outside the allowable range, as shown in FIG. 11, a message window $W_{12}$ is displayed, and a message $M_8$ "VALIDATION FAULT" is displayed on the window screen while an announcement by speech is being outputted (step $S_{t13}$).

Figure 11:
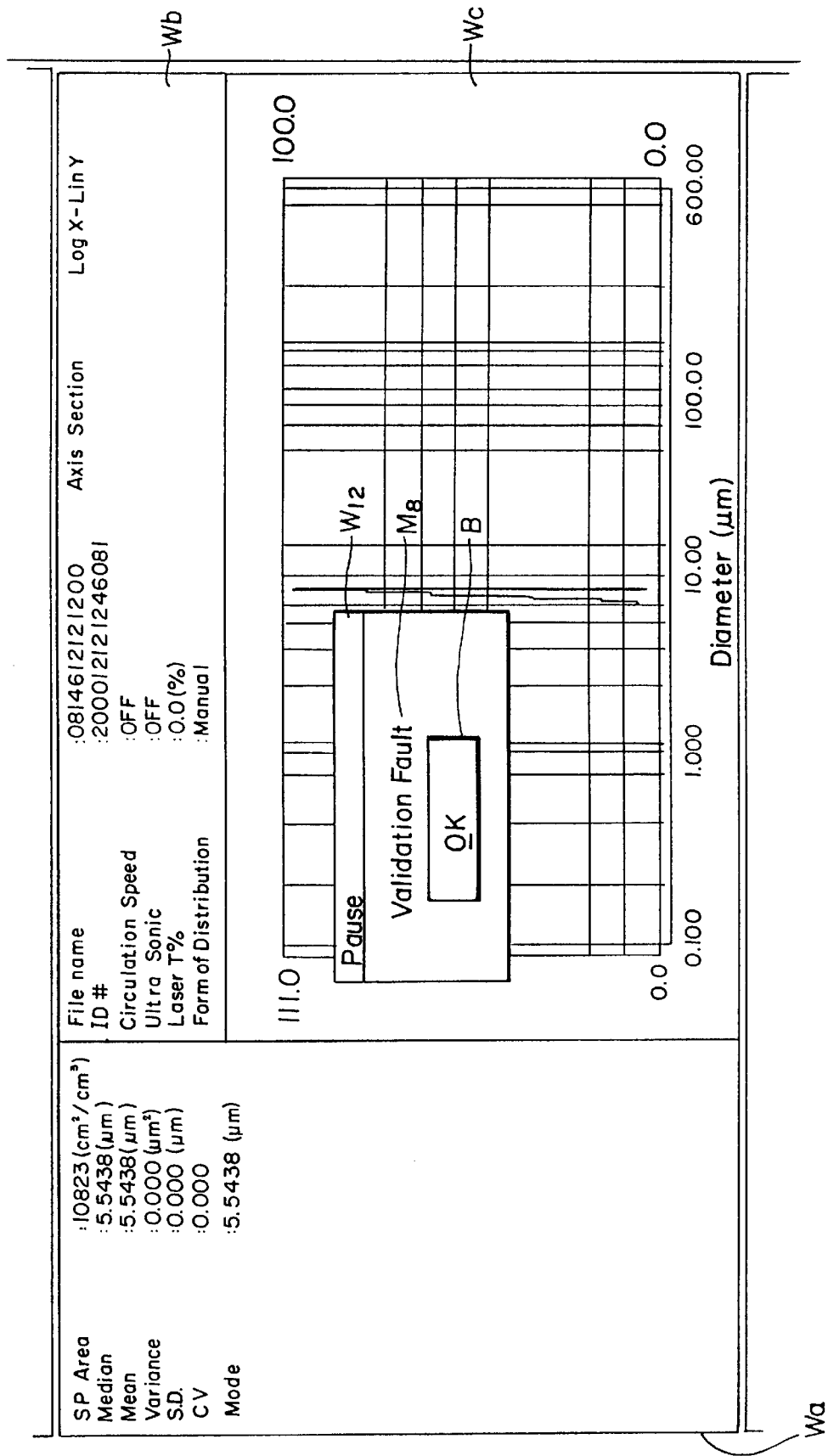
FIG. 11 is a view showing another display window on the screen.
Figure 12:
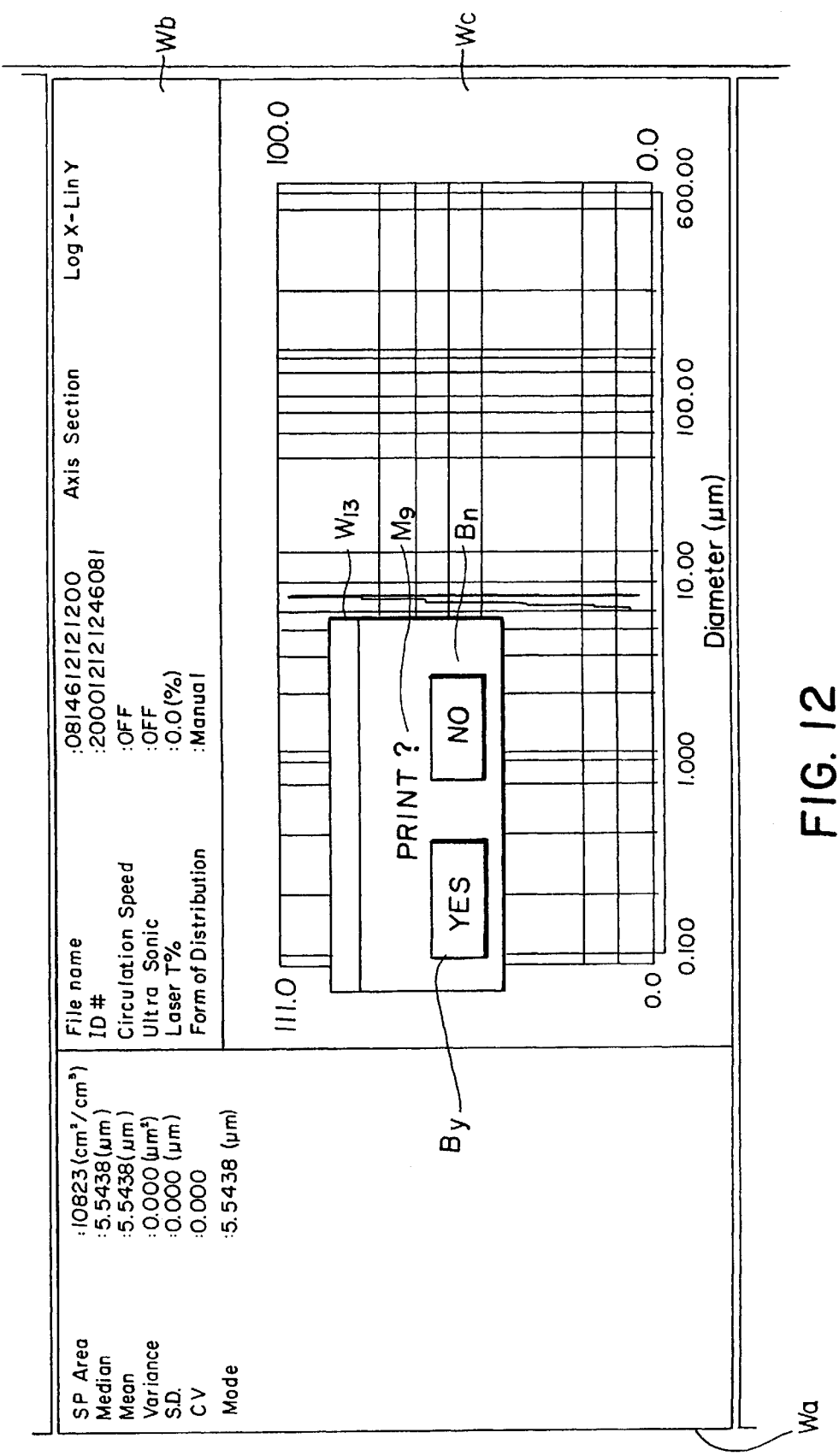
FIG. 12 is a view showing another display window on the screen.

In each case, when the operator presses the OK button B shown in FIG. 10 and FIG. 11, the personal computer 3 displays a message window $W_{13}$ as shown in FIG. 12, and then, displays a message $M_9$ "PRINT?" on the window screen while outputting the same announcement by speech (step $S_{t14}$).

When the operator presses a "YES" button By, the personal computer 3 prints inspection results such as measured result, validation standards, measuring person's name, date and time, kind of measuring apparatus, operational parameters or the like via a printer (not shown) (step $S_{t15}$). Namely, the operator can determine whether the result should be printed when performing the validation work; therefore, the operator never forgets to record the validation work.

On the other hand, in the window $W_{13}$ shown in FIG. 12, when the operator presses a "NO" button Bn, the personal computer 3 does not perform any procedure, and then, executes the next procedure (step $St_{t16}$).

FIG. 13 shows an example of the next step $S_{t16}$. In this embodiment, the personal computer 3 displays a window $W_{14}$ for recording inspection results such as measured result, validation standards, measuring person's name, date and time, the kind of measuring apparatus, and operational parameters in a storage section $3m$ as digital data. The window $W_{14}$ has an input bar N, an input bar F, a list L, a save button Bs for executing a save, and a cancel button Bc for canceling a save. More specifically, the input bar N is used for setting a file name for adding a file bundling a saving data, and the input bar F is used for setting a folder saving the file, and further, the list L is used for displaying a file name list of the file already stored in the folder.

Therefore, the operator can input a folder and a file name by using the above input bars F and N (step $S_{t16}$). The operator presses the save button Bs, and thereby, it is possible to readily save the inspection result (step $S_{t17}$).

On the other hand, when the operator presses the cancel button Bc, the saving of the inspection result is cancelled, and the validation work ends.

The aforesaid embodiment is merely one embodiment of the present invention, and therefore, the present invention is not limited to this embodiment. More specifically, in the above embodiment, respective contents of the messages $M_1$ to $M_9$ displayed on each of the windows $W_5$ to $W_{13}$ may be announced by speech (voice), and thereby, the operator can extremely readily obtain validation help from the personal computer 3. The present invention is not limited to this modification and the message may be made by either of display on the display screen $3d$ or announced by speech.

Likewise, this embodiment has disclosed the case of printing the inspection result record on a paper and the case of storing it in a file as a digital data. Either of two disclosures may be carried out. Moreover, the inspection result record may be separately carried out by the operator.

In the above embodiment, as shown in the window $W_2$ of FIG. 3, three parameter values (median diameter, 10% diameter, 90% diameter) are set with respect to one standard sample S as validation standards. The present invention is not limited to this embodiment. For example, a geometrical mean particle diameter or the like may be set.

Further, the standard sample S to be measured is not limited to one kind.

Figure 14:
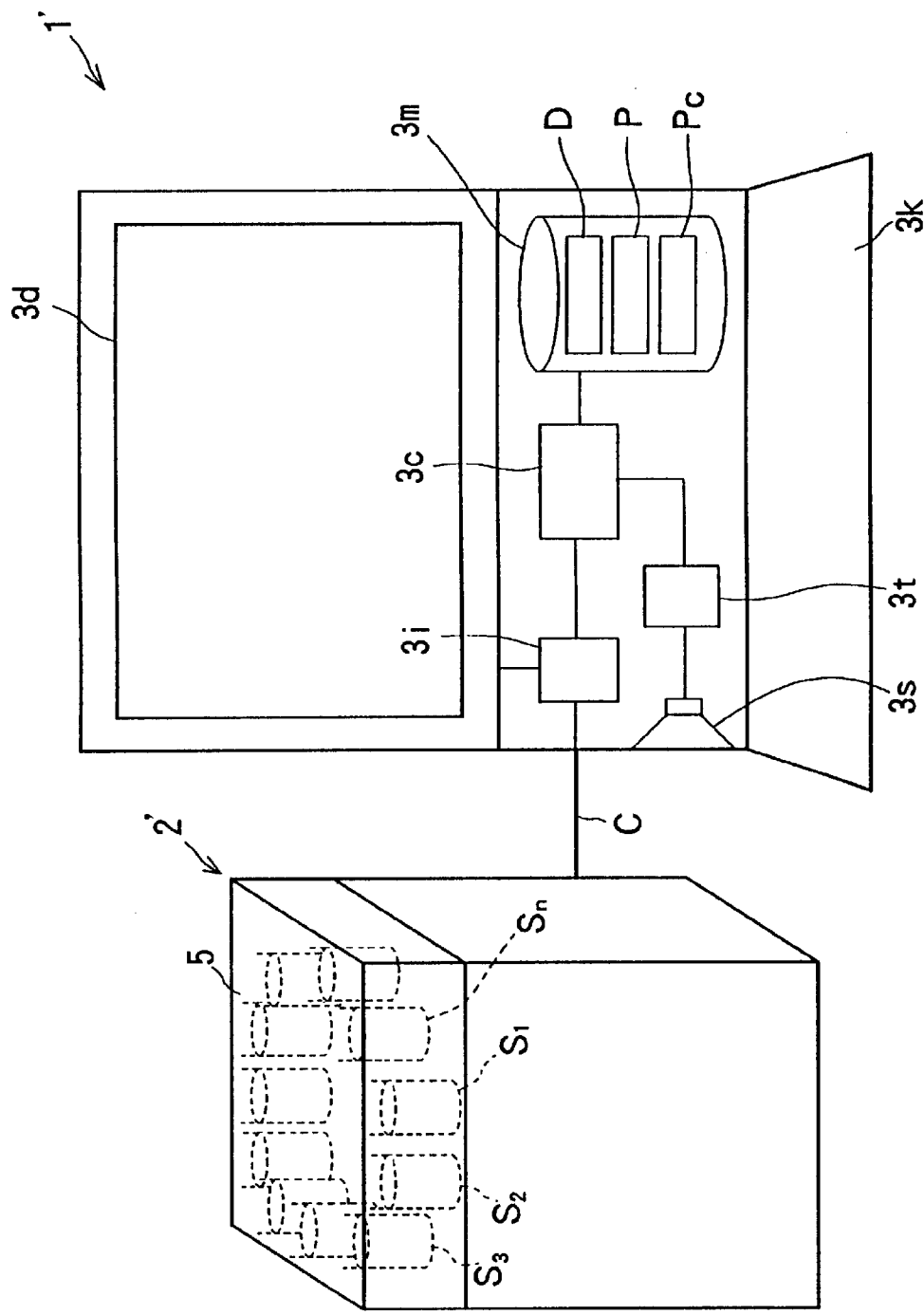
FIG. 14 is a view showing a particle size distribution measuring apparatus according to another embodiment.

FIG. 14 is a view showing a particle size distribution measuring apparatus according to another embodiment of the present invention. A particle size distribution measuring apparatus 1' will be described below with reference to FIG. 14. In the particle size distribution measuring apparatus 1', like reference numerals are used to designate the same member as FIG. 1, and therefore, the details are omitted.

In this embodiment, a reference numeral 2' denotes a measuring section for measuring a particle size distribution of measuring an object sample. The measuring section 2' is different from the measuring section 2 detailed described in FIG. 1 in that it 2' has an automatic sample charger 5 for automatically charging a plurality of standard samples $S_1$ to $S_n$ according to the control by the personal computer 3.

Figure 15:
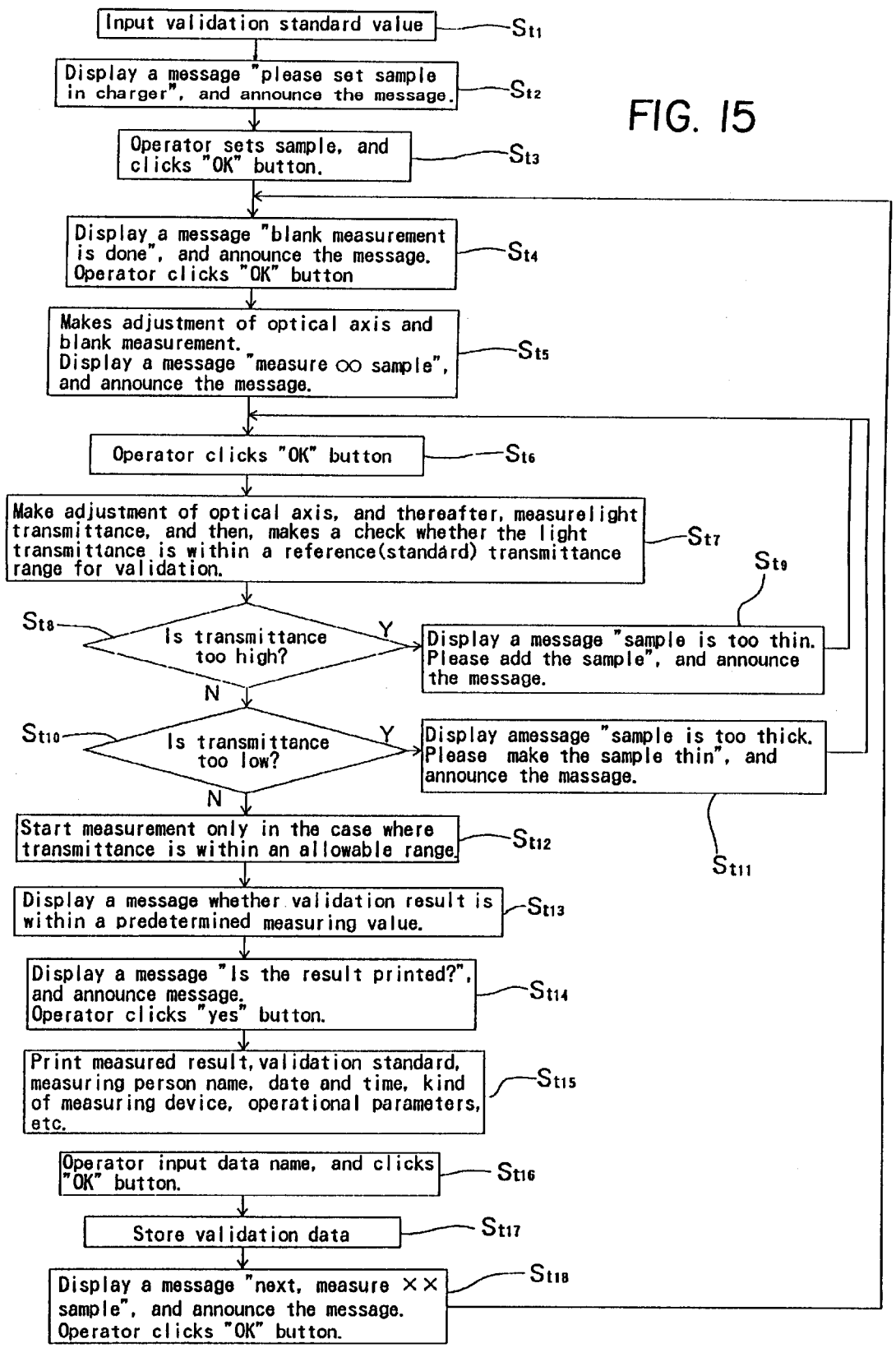
FIG. 15 is a view to explain an operation of the validation help function of the above embodiment.
Figure 16:
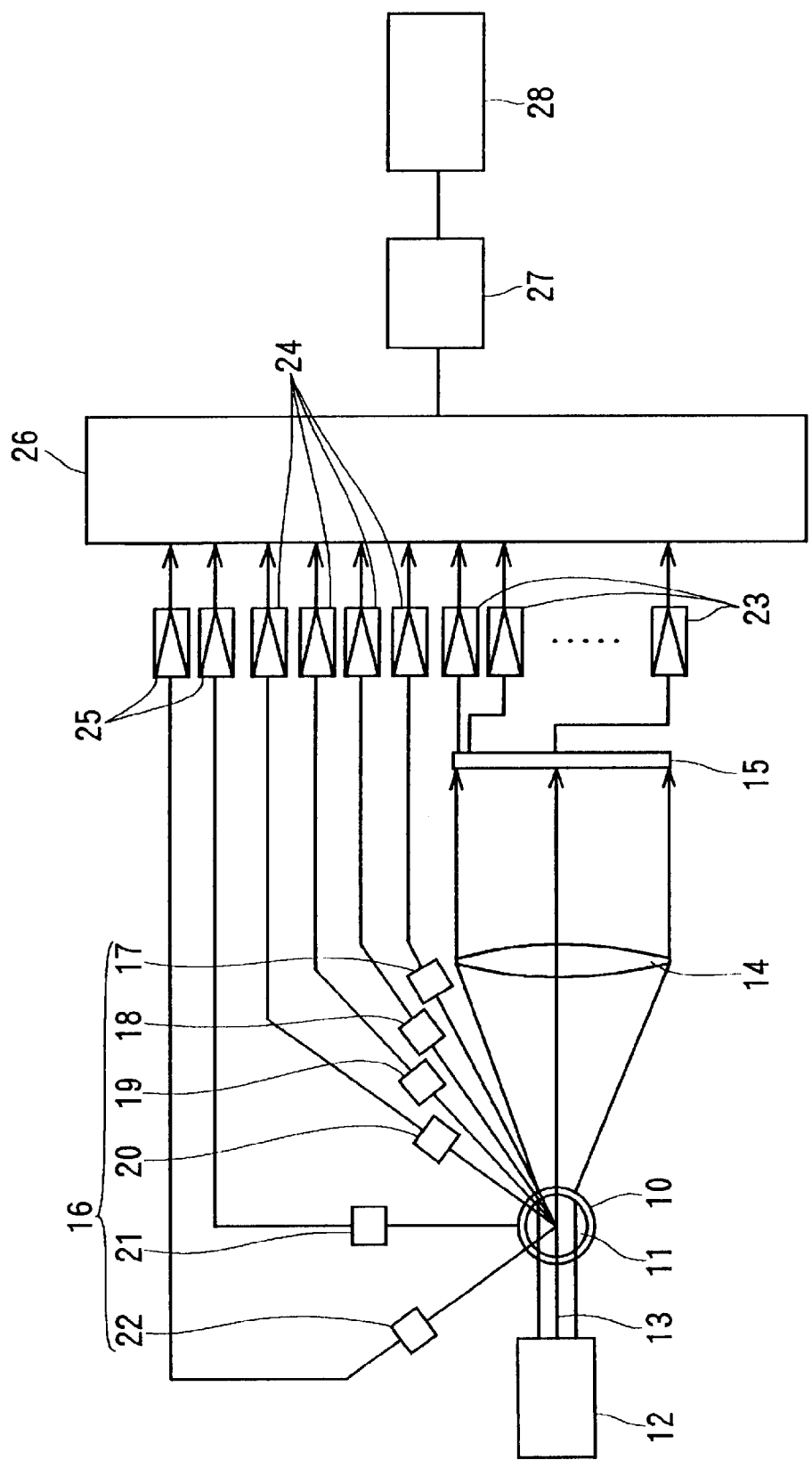
FIG. 16 is a view to explain the measuring principle of a conventional particle size distribution measuring apparatus.

FIG. 15 is a flowchart showing a procedure of validation work performed according to the control of the particle size distribution measuring apparatus 1'. In FIG. 15, the same steps $S_{t1}$ to $S_{t17}$ as FIG. 2 have almost the same description as FIG. 2, and therefore, the details are omitted for simplification of description.

In each procedure shown in FIG. 15, the procedures which are different from the description of FIG. 2 is as follows. More specifically, in step $S_{t3}$, standard samples $S_1$ to $S_n$ are set with respect to the automatic sample charger 5, and there is no need of making a message displayed in step $S_{t5}$ and charging a sample by the operator in step $S_{t6}$.

Moreover, in this embodiment, the following step $S_{t18}$ for making a confirmation by the operator is added. More specifically, when measurement of one sample is completed, a message "next, measure another sample" is displayed on the screen, and then, announce by speech is made. In this case, when the operator presses the OK button, the personal computer 3 controls the automatic sample charger 5 so as to charge the next sample, and then, the procedures from step $S_{t4}$ is repeatedly made.

In this embodiment, when the procedure jumps from step $St_{18}$ to step $S_{t4}$, a blank measurement is made when the standard samples $S_1$ to $S_n$ are changed in succession, and thereby, a measurement accuracy is improved. The present invention is not limited to this embodiment. For example, the procedure jumps from step $S_{t18}$ to step $S_{t7}$, and thereby, measurement may be made at a high speed.

As is evident from the above description, by using the particle size distribution measuring apparatus of the present invention, when the operator performs a validation work, the operator can receive a suitable validation help. More specifically, by validation help function, it is possible to operate the particle size distribution measuring apparatus according to a work procedure given from a control unit in a predetermined order without making a mistake. Moreover, a measurement procedure controlled by only control unit is automatically made according to a sequence of the measurement procedure previously stored as a validation data. Therefore, the operator can perform the complicated validation work without referring to a manual, so that a load acting on the operator can be reduced to the minimum. In addition, the work procedure is executed by one step without making a mistake, so that the validation work can be accurately performed.

What is claimed is:

1. A particle size distribution measuring apparatus comprising:

a storage medium storing validation data for validating the performance of a particle size distribution measuring apparatus; and a control unit for providing validation help function which
successively reads a validation procedure from the validation data, and
successively carries out control of the particle size distribution measuring apparatus according to a measuring procedure requiring
no operation by an operator in the validation procedure, and when operator intervention is necessary,
providing step-by-step validation instructions to the operator of a work procedure requiring an operation by the operator, wherein at least one of the operations requires the operator to provide one or more parameters for validating the measuring apparatus.

2. The particle size distribution measuring apparatus according to claim 1, and wherein the control unit includes a warning function of pointing out the operator's mistake in the work procedure to the operator, and teaching a validation work according to a correct work procedure.

3. The particle size distribution measuring apparatus according to claim 1, wherein the control unit includes a speech output section for outputting an instruction to the operator by an audio signal.

4. The particle size distribution measuring apparatus according to claim 1, wherein the control unit has a monitor screen for displaying an instruction to the operator.

5. The particle size distribution measuring apparatus according to claim 1, further including an automatic charger for successively charging a standard sample used for the validation work in the particle size distribution measuring apparatus.

6. The particle size distribution measuring apparatus according to claim 1, wherein the control unit includes a judgment function of comparing an inspection result obtained from the validation work with a performance standard of the particle size distribution measuring apparatus, and making a judgment whether the comparative result is within a predetermined performance standard range.

7. The particle size distribution measuring apparatus of claim 1, wherein the control unit includes a recording function of recording the inspection result obtained by the validation work.

8. A The particle size distribution measuring apparatus of claim 1 wherein providing step-by-step validation instructions to the operator includes, requesting that the operator provide a predetermined standard sample with which to validate the measuring apparatus.

9. In an improved particle size distribution measuring apparatus having a measuring section for receiving a sample, a source of light for irradiating the sample and sensors for measuring the light after irradiating the sample, the improvement comprising:

a validation unit for determining the accuracy of measurements when a predetermined standard is irradiated in the measuring section; and an instructing unit for providing step-by-step validation instructions to an operator as the validation unit performs the measurements of the predetermined standard, wherein at least one of the instructions requires the operator to provide one or more parameters for validating the measuring apparatus.

10. The particle size distribution measuring apparatus of claim 9 further including an automatic sample standard unit for inserting the predetermined standard into the measuring section.

11. The particle size distribution measuring apparatus of claim 9 further including a speaker wherein the instructions are generated as audible speech to the operator.

12. A particle size distribution measuring apparatus capable of interactive calibration procedures to guide a user, comprising:

a measuring section for receiving a sample;

a source of light for irradiating the sample;

a sensor unit for measuring the light after irradiation and providing measurement signals;

a measuring unit for storing reference values to enable calibration;

a controller for processing the measurement signals to measure particle sizes;

a display screen;

a user interface unit;

a validation program stored in the memory unit to enable the controller to validate the performance of the particle size distribution measuring apparatus including displaying a series of predetermined screens with indicia to prompt a response from a user on the user interface unit;

means for prompting a user to insert a calibration sample into the measurement section;

means for adjustment of an optical axis between the measuring section and the source of light;

automatic means for measuring light transmittance through the measuring section;

means for comparing the light transmittance measurement with stored reference values to determine when the measurement is one of a value above the stored reference values and below the stored reference values when the calibration sample is in the measurement section; means for displaying a message to prompt the user to alter the calibration sample when one of a value above the stored reference values and below the stored reference values is measured; and means for displaying a message that the validation result is within the stored reference values wherein the user is directed through the validation procedures by displayed indicia and by automatic procedures initiated directly by the controller.

13. The particle size distribution measuring apparatus of claim 12 further including a monitoring sensor to determine if the measuring section is open and means to display a message to close the measuring section.

14. The particle size distribution measuring apparatus of claim 12 further including means to display a message to insert dispersion medium in the measuring section.

* * * * *